United States Patent [19]

Nedetzky

[11] 4,358,423
[45] Nov. 9, 1982

[54] METHOD AND APPARATUS FOR MONITORING AND CONTROLLING THE CHARGING OPERATION OF AN ELONGATED MEASURING CHAMBER

[75] Inventor: Walter Nedetzky, Graz, Austria

[73] Assignee: AVL AG, Schaffhausen, Switzerland

[21] Appl. No.: 234,136

[22] Filed: Feb. 13, 1981

Related U.S. Application Data

[63] Continuation of Ser. No. 961,432, Nov. 16, 1978, abandoned.

[30] Foreign Application Priority Data

Nov. 16, 1977 [CH] Switzerland ............... 14017/77

[51] Int. Cl.³ .................. G01N 35/00; G01N 27/00
[52] U.S. Cl. .................... 422/68; 23/230 A; 422/81
[58] Field of Search .............. 422/68, 100, 81; 23/230 A; 324/65 R, 65 P

[56] References Cited

U.S. PATENT DOCUMENTS

| 3,367,849 | 2/1968 | Blaedel et al. | 422/81 |
| 3,556,950 | 1/1971 | Dahms | 23/230 R |
| 3,884,640 | 5/1975 | Lock | 422/68 |

FOREIGN PATENT DOCUMENTS

| 60304 | 1/1913 | Austria . |
| 958422 | 5/1964 | United Kingdom . |
| 1061759 | 3/1967 | United Kingdom . |
| 1343767 | 1/1974 | United Kingdom . |
| 1465417 | 2/1977 | United Kingdom . |

Primary Examiner—Michael S. Marcus
Attorney, Agent, or Firm—Ladas & Parry

[57] ABSTRACT

A measuring chamber contains contact devices between each of which the electric resistance is measured before the actual analysis of the blood gases begins so that erroneous measurements are avoided if the measuring chamber is not completely filled with a blood specimen or to enable blood gas analysis to be carried out with small quantities of specimen material.

3 Claims, 1 Drawing Figure

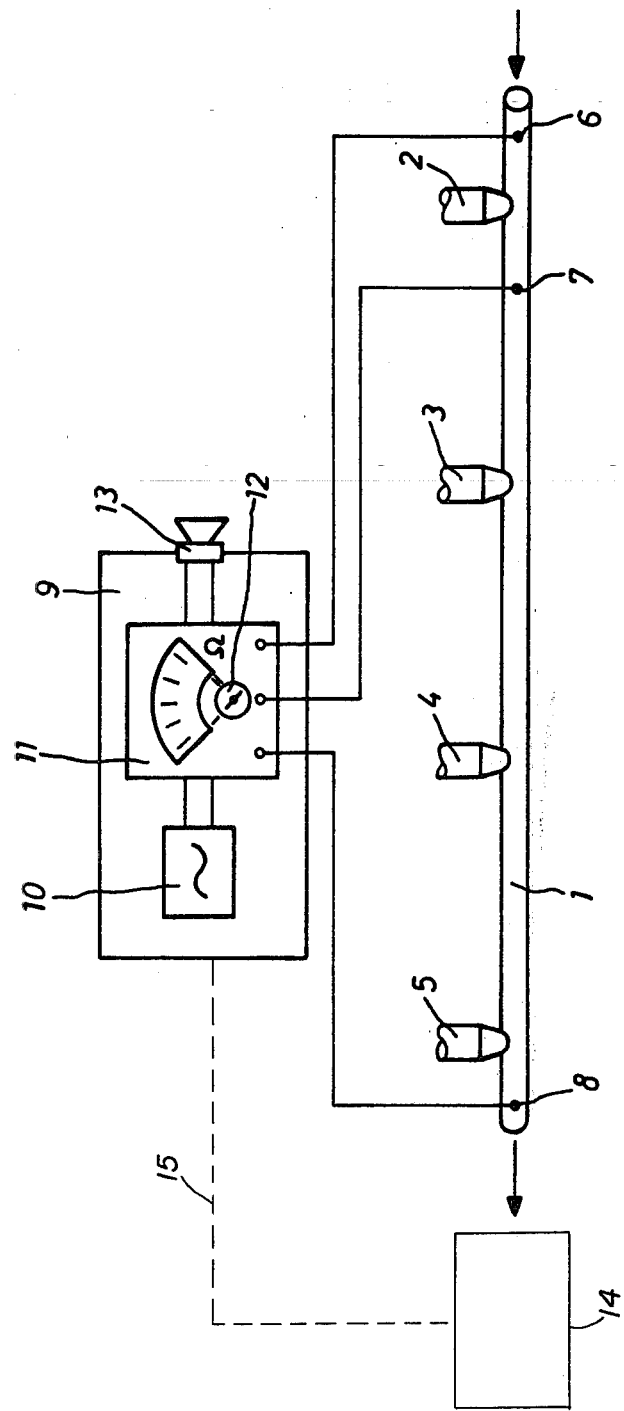

METHOD AND APPARATUS FOR MONITORING AND CONTROLLING THE CHARGING OPERATION OF AN ELONGATED MEASURING CHAMBER

This is a continuation of co-pending Application Ser. No. 961,432 filed Nov. 16, 1978, now abandoned.

The present invention relates to a method for monitoring and controlling the charging operation of an elongated measuring chamber containing a liquid specimen material and the measuring chamber is provided with selective measuring electrodes, also to apparatus for performing the said method.

It is necessary in blood gas analyzers to monitor the procedure of charging the measuring chamber with the liquid specimen material which is to be investigated and to monitor the state of charge of the measuring chamber. With the results obtained thereby it is possible to control the operation of charging the measuring chamber which is usually of capillary form and has selective measuring electrodes extending therein.

After the entire measuring chamber is completely charged with the specimen material it is necessary to interrupt any further supply of specimen material and to initiate the actual measuring procedure by means of the selective measuring electrodes.

The presence of air bubbles in the liquid specimen material already disposed in the elongated measuring chamber can lead to measuring results which do not represent the actual properties of the specimen material. This is because air bubbles prevent the relevant selective electrodes being properly wetted with the specimen material. Accordingly, it is necessary to provide steps by means of which such a state is recognized in good time so that the bubbles can be removed from the blood gas analyzer, for example by displacing the entire liquid column in the capillary measuring chamber and by supplying additional specimen material.

In automatically operating blood gas analyzers, in which the person operating the same does not inspect the procedure of charging measuring chamber, it is also necessary for the operation of charging the measuring chamber to be performed under automatic inspection.

The problems and requirements in the method of the initially-mentioned kind are solved in accordance with the invention in that the value of the resistance between at least two places in the measuring chamber is measured and that the procedure of charging the measuring chamber with the specimen material is controlled in dependence of the measured magnitude of the resistance value. The apparatus according to the invention for performing this method is characterised in that it comprises at least two contact devices extending into the interior of the measuring chamber and adapted to come into contact with the specimen material and that the said contact devices are connected to a monitoring device which measures the value of the resistance of the distance within the measuring chamber between the two contact devices and generates and transmits corresponding signals.

Embodiments of the present invention will be explained by reference to the accompanying drawing.

The apparatus for performing the present method is shown diagrammatically in the said drawing. The subject of the drawing can in some circumstances also be part of an automatic blood gas analyzer.

Since the individual parts of a blood gas analyzer are well known the accompanying drawing shows only that part thereof which has been modified to a certain extent to enable the above-mentioned method to be performed.

The present invention comprises a measuring chamber 1 which is capillary in the present case. A device 14 is provided for drawing specimen material into the chamber. Selective measuring electrodes 2 to 5 are inserted in the wall of the measuring chamber 1 and are distributed over the entire length of the measuring chamber 1 which is constructed as capillary tube, namely from its beginning, where the specimen material is charged, to its end, where the specimen material is discharged.

The first measuring electrode 2 can be a pH reference electrode and the second measuring electrode can be a pH sensitive gas electrode. The third electrode 4 can be constructed as a $CO_2$ sensitive electrode to measure the partial pressure of $CO_2$ dissolved in blood. Finally, the fourth measuring electrode attached to the capillary tube 1 can be an electrode which is sensitive to oxygen. Such measuring electrodes are connected to evaluating circuits for the individual measured values, which said circuits are not shown in the accompanying drawing but are well known to experts.

The capillary measuring chamber 1 is also provided with three contacts or contact members 6 to 8 which are disposed in the interior of the capillary 1 or at least extend therein. In this manner the contact members 6 to 8 can come into conductive connection with the material of the liquid specimen if the said specimen material is disposed in the measuring chamber 1. As can be seen by reference to the drawing the first contact device 6 is disposed at the very beginning of the capillary tube where the liquid specimen is supplied. The second contact device 7 is disposed downstream of the first measuring electrode 2 which extends into the capillary tube. The third contact device 8 on the other hand is disposed at the end of the capillary tube 1 where the liquid specimen material emerges from the measuring chamber.

In pricniple it will be sufficient if only two of the three above-mentioned contact devices were to be provided. However, the use of the three contact devices in the system illustrated in the drawing appears to be most convenient.

A further modification of this device can be constructed so that one of the measuring electrodes also functions as one of the contact devices. More particularly this can be the pH reference electrode 2 which need not however necessarily be disposed at the beginning of the measuring chamber. This dispenses with the need of working one of the above-mentioned contact members 6 or 7 or 8 into the wall of the capillary glass tube 1.

The individual contact devices will then be connected to a monitoring device 9. The said monitoring device 9 contains an alternating voltage source 10 which can be connected by means of an ohm meter 11 to the individual contact devices, for example 6 to 8. The monitoring device 9 controls operation of the device 14, as indicated diagramatically by the connection 15.

The drawing shows a resistance meter which is provided with a changeover switch 12 by means of which one pair of contacts at a time, either the pair of the contacts 6 and 7 or the pair of the contacts 7 and 8 can be connected to the measuring system of the ohm meter 11. As can be seen the middle contact member forms the common reference point for the two contact pairs and the state of charge of the measuring chamber formed by the capilalary tube 1 is monitored by means of these three contacts.

If the capillary is correctly charged an electrically conductive bridge will first be established between contacts 6 and 7. Furthermore, an electrical connection will also be established between contacts 7 and 8. The establishment of the last-mentioned electrical connection between contacts 7 and 8 is utilized for interrupting any further drawing-in of measuring fluid into the measuring chamber 1 because the capillary measuring tube will be filled and the actual procedure of blood gas analysis can then proceed.

If the charge in the measuring chamber 1 contains air bubbles the electrical connection between the contacts 6 and 7 will probably also be established but will again be interrupted by the enclosed air bubbles before the distance between contacts 7 and 8 become electrically conductive. This effect is utilized to interrupt the charging operation and to signal a breakdown. To this end the monitoring device can be provided with a signalling device 13, for example with an audible signalling device or where appropriate only with an optical signalling device (not shown). In this way it is possible to avoid erroneous measurements if air bubbles are present in the blood specimen. In this way it is also possible to obtain measured values from all measuring electrodes with liquid quantities which are insufficient for complete charging of the measuring chamber 1. This is because after a fault has been signalled and a charging operation has been interrupted the liquid column already disposed in the capillary tube will be successively advanced under each seat of the measuring electrodes 3, 4 or 5.

I claim:

1. Apparatus for analyzing liquid specimen material, comprising wall means defining an elongated measuring chamber, means for introducing liquid specimen material into said chamber, a plurality of selective measuring electrodes extending through said wall means for contacting the specimen material and sensitive to predetermined characteristic of the specimen material for providing output measurements suitable for analysis, three spaced electrically conducting contact devices extending through said wall means for also contacting the specimen material, the first contact device being located at the input end of said chamber, the second contact device being located downstream of one of said electrodes and upstream of the other electrodes, and the third contact device being located at the output end of said chamber, and inluding a monitoring device connected to said three contact devices for measuring the electrical resistance through the specimen material between respective contact devices and generating corresponding signals, said means for introducing the specimen material being responsive to said signals for controlling the flow of the specimen material in said chamber.

2. Apparatus according to claim 1 in which at least one of said selective measuring electrodes also functions as a contact device.

3. Apparatus according to claim 1 in which said second contact device functions as a common contact for said first and third contact devices.

* * * * *